United States Patent
Robinson

(10) Patent No.: US 9,278,011 B2
(45) Date of Patent: Mar. 8, 2016

(54) PERCUTANEOUS CAGE DELIVERY SYSTEMS DEVICES AND METHODS

(71) Applicant: James C. Robinson, Atlanta, GA (US)

(72) Inventor: James C. Robinson, Atlanta, GA (US)

(73) Assignee: SPECTRUM SPINE IP HOLDINGS, LLC, Atlanta, GA (US)

( * ) Notice: Subject to any disclaimer, the term of this patent is extended or adjusted under 35 U.S.C. 154(b) by 0 days.

(21) Appl. No.: 13/962,501

(22) Filed: Aug. 8, 2013

(65) Prior Publication Data

US 2014/0046446 A1 Feb. 13, 2014

Related U.S. Application Data

(60) Provisional application No. 61/680,729, filed on Aug. 8, 2012.

(51) Int. Cl.
*A61F 2/44* (2006.01)
*A61F 2/46* (2006.01)
*A61F 2/30* (2006.01)

(52) U.S. Cl.
CPC .............. *A61F 2/4611* (2013.01); *A61F 2/447* (2013.01); *A61F 2002/30179* (2013.01); *A61F 2002/30784* (2013.01); *A61F 2002/30785* (2013.01); *A61F 2002/4475* (2013.01); *A61F 2002/4677* (2013.01)

(58) Field of Classification Search
CPC .................... A61F 2/4611; A61F 2/44–2/4475
USPC .............. 606/279, 99, 105; 623/17.11–17.16
See application file for complete search history.

(56) References Cited

U.S. PATENT DOCUMENTS

| | | | | |
|---|---|---|---|---|
| 6,652,533 B2 * | 11/2003 | O'Neil | | 606/100 |
| 7,615,079 B2 * | 11/2009 | Flickinger et al. | | 623/17.16 |
| 8,034,110 B2 * | 10/2011 | Garner et al. | | 623/17.11 |
| 2002/0055745 A1 * | 5/2002 | McKinley et al. | | 606/99 |
| 2003/0149438 A1 * | 8/2003 | Nichols et al. | | 606/99 |
| 2006/0149245 A1 * | 7/2006 | Sweeney | | 606/61 |
| 2006/0276899 A1 * | 12/2006 | Zipnick et al. | | 623/17.13 |
| 2006/0293756 A1 * | 12/2006 | Felt | | 623/17.16 |
| 2007/0050036 A1 * | 3/2007 | Felt et al. | | 623/17.16 |
| 2008/0234687 A1 * | 9/2008 | Schaller et al. | | 606/90 |
| 2009/0171389 A1 * | 7/2009 | Sankaran | | 606/246 |
| 2010/0286695 A1 * | 11/2010 | Hannani et al. | | 606/80 |
| 2011/0230965 A1 * | 9/2011 | Schell et al. | | 623/17.11 |
| 2011/0282459 A1 * | 11/2011 | McClellan et al. | | 623/17.16 |
| 2012/0123465 A1 * | 5/2012 | Nihalani | | 606/192 |
| 2013/0138214 A1 * | 5/2013 | Greenhalgh et al. | | 623/17.16 |
| 2013/0245770 A1 * | 9/2013 | Felt et al. | | 623/17.16 |

* cited by examiner

*Primary Examiner* — Eduardo C Robert
*Assistant Examiner* — Michelle C Eckman
(74) *Attorney, Agent, or Firm* — FisherBroyles, LLP; Anthony J. DoVale

(57) ABSTRACT

An insertion guide to aid in placing a cage into an intervertebral space is presented. The insertion guide has an elongate insertion member having a cross-sectional shape configured to engage a portion of the cage. An end of the insertion member is positioned in a desired location in the intervertebral space and the cage slides along the length of the insertion member to the desired location.

18 Claims, 3 Drawing Sheets

PERCUTANEOUS CAGE DELIVERY SYSTEMS DEVICES AND METHODS

CROSS REFERENCE TO RELATED APPLICATIONS

This application is a Non-Provisional of U.S. patent application 61/680,729, filed Aug. 8, 2013, which is incorporated in its entirety in this document by reference.

BACKGROUND

The following disclosure relates generally to medical devices, systems and methods, including, for example, systems and methods for lumbar interbody fusion.

Surgical implantation of disc replacement material is typically used to provide support along the spinal column in cases where a portion of the patient's intervertebral anatomy has become weakened, diseased, or destroyed. Such support systems are also commonly used following a discectomy, where an intervertebral disc is surgically removed.

Most commonly, existing support systems typically operate by inhibiting normal movement between the adjacent vertebrae, thereby holding these vertebrae at fixed positions relative to one another, with the mechanical body of the supporting structure providing the needed support along the patient's spinal column. Such supporting systems are typically made of stainless steel, titanium, polymer (e.g., an organic polymer thermoplastic such as polyether ether ketone (PEEK)), carbon fiber, or ceramic and they are designed to permanently remain within the patient's body.

It is beneficial, in addition to fixation, to try to stimulate bone growth between the adjacent vertebrae. To do so, spine surgeons use bone graft material in addition to fixation devices. Bone graft doesn't heal or fuse the spine immediately; instead, bone graft provides a foundation or scaffold for the patient's body to grow new bone. Bone graft can stimulate new bone production. When new bone grows and solidifies, fusion occurs. Although instrumentation (e.g., screws, rods) is often used for initial stabilization (post-operative), it is the healing of bone that welds vertebrae together to create long-term stability. There are two general types of bone grafts: real bone and bone graft substitutes. Real bone can come from the patient (autograft) or from a donor bone (allograft). Also used in these types of surgery are bone substitute, osteoinductive agent, and bone cement.

There is a need for improved systems and methods for lumbar interbody fusion.

SUMMARY

An insertion guide to aid in placing an intervertebral cage into an intervertebral space is disclosed. The insertion guide can allow a user to place the cage into a desired location and at a desired orientation.

In one aspect, the insertion guide comprises an elongate insertion member having a proximal end and a distal end. The insertion member can be sized and shaped in cross-section to matingly engage a channel and/or an opening defined in the cage assembly. That is, the insertion member can have a cross-sectional size and shape such that the intervertebral cage can be slidably coupled to the insertion member. In use, the distal end of the insertion member can be positioned in the desired location in the intervertebral space and the proximal end of the insertion member can be inserted into the channel of the intervertebral cage. The intervertebral cage can then be urged along the length of the insertion member to the desired location in the intervertebral space.

In another aspect, the insertion guide further comprises a Kirschner wire ("guide wire") having a distal end, a longitudinal length and a cross-sectional profile. A longitudinal bore can be defined in the insertion member such that the bore extends from the proximal end to the distal end of the insertion member. In this aspect, the cross-sectional profile of the bore can be similar to the cross-sectional profile of the guide wire so that the insertion member can be slidably coupled to the guide wire. In use, the distal end of the guide wire can be positioned in the desired location in the intervertebral space and the opposed end of the guide wire can be inserted into the bore of the insertion member. The insertion member can then be urged along the length of the guide wire to position the distal end of the insertion member in the desired location in the intervertebral space. The intervertebral cage can then be slidably coupled to the insertion member as previously described.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

These and other features of the preferred embodiments of the present invention will become more apparent in the detailed description in which reference is made to the appended drawings wherein.

DETAILED DESCRIPTION

Figure 1:
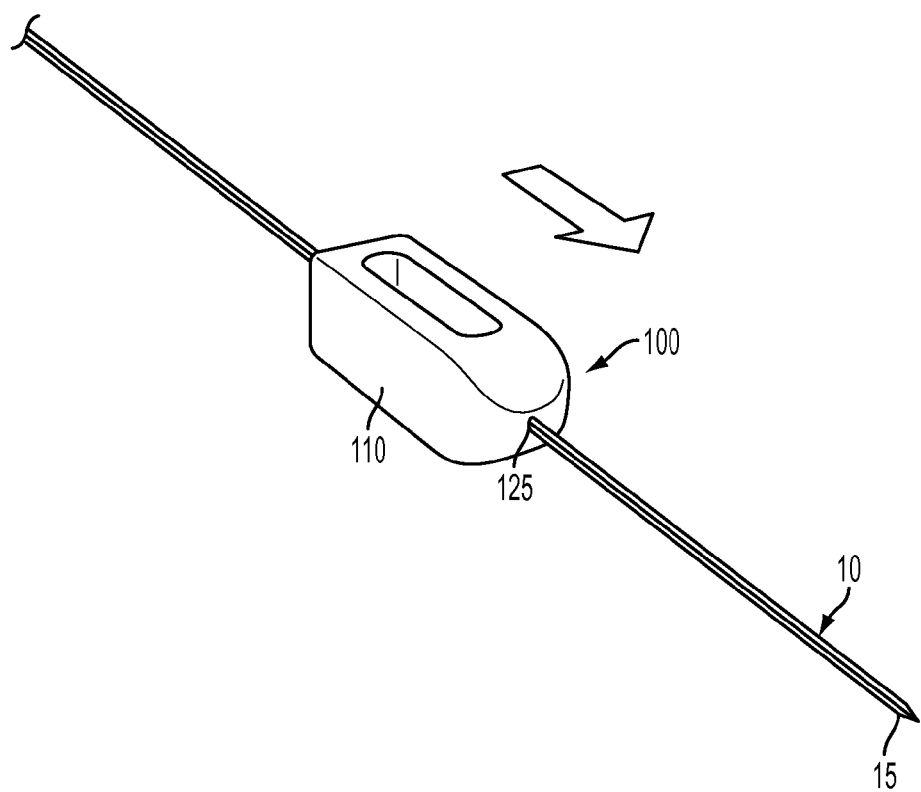
FIG. 1 is a perspective view of an intervertebral cage delivered over a Kirschner wire, according to various aspects.

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a" component can include two or more such components unless the context indicates otherwise. Also, the words "proximal" and "distal" are used to describe items or portions of items that are situated closer to and away from, respectively, a user or operator such as a surgeon. Thus, for example, the tip or free end of a device may be referred to as the distal end, whereas the generally opposing end or handle may be referred to as the proximal end.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Presented herein are systems, tools, and methods for supporting adjacent vertebrae of the spine, for example, as part of interbody spinal fusion surgery. Intervertebral cages are used in spinal fusion surgery to increase space and/or lordosis in a human subject. Cages, in general, are used in oblique lateral interbody fusion (OLIF) procedures, transforaminal lumber interbody fusion procedures (TLIF), direct lumber interbody fusion procedures (DLIF), and the like. For illustrative purposes only, we describe the intervertebral cage as a generic OLIF cage herein, although the insertion member described herein can be used with almost any type of intervertebral cage. In one aspect, the intervertebral cage defines a longitudinal aperture, pathway, or bore.

In one aspect, an intervertebral cage 100 may be inserted using a minimally invasive delivery system that comprises an insertion member 400, 500 and/or a guide wire 10, such as, for example and without limitation, a Kirschner wire (K-wire). The intervertebral cage can have a cage body 110 defining an interior longitudinal channel 120 extending from a distal opening to a proximal opening of the intervertebral cage. The distal opening can have an opening profile and the longitudinal channel can have a cross-sectional shape. The delivery system may be used, for example, to conduct a minimal-access oblique extra-foramenal lumbar interbody fusion. A guide wire may be inserted, with guidance, into the disc space in the triangular extra-foramenal safe zone, followed by a reamer. In one aspect, the intervertebral cage 100 may be delivered over the guide wire 10, as shown in FIG. 1.

In another aspect, the insertion member 400, 500, either alone or in combination with the guide wire 10, can be used to deliver the intervertebral cage 100 to the desired location, as illustrated in FIGS. 2, 3, 4 and 5. The insertion member 400, 500 can have a longitudinal axis and cross-sectional shape or profile. In one aspect, the cross-sectional profile of the insertion member can be similar (i.e., having the same shape, though not the same size) to an opening profile of the distal opening of the cage body 110 when viewed in elevation and/or a cross-sectional shape of the interior longitudinal channel 120 of the cage body 100. That is, when viewing the cage body in, for example, a side elevational view, the distal opening of the cage body can have a shape that is similar to a cross-sectional shape of the insertion member 400, 500. In another aspect, the insertion member 400, 500 can have a cross-sectional profile slightly smaller than the elevational shape of the distal opening of the cage body 110 so that at least a portion of the insertion member can slide through the distal opening (and the interior channel 120) of the cage body 110.

Figure 2:
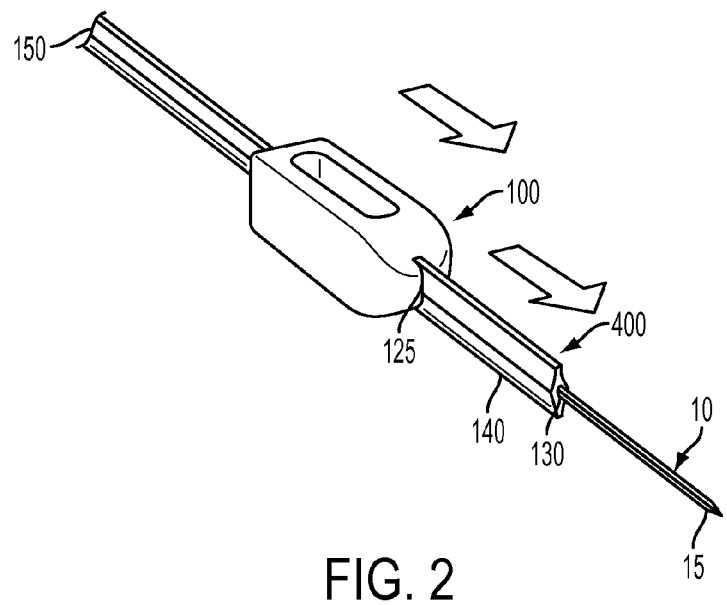
FIG. 2 is a perspective view of an intervertebral cage delivered over an insertion member, placed over a Kirschner wire, according to various aspects.
Figure 4:
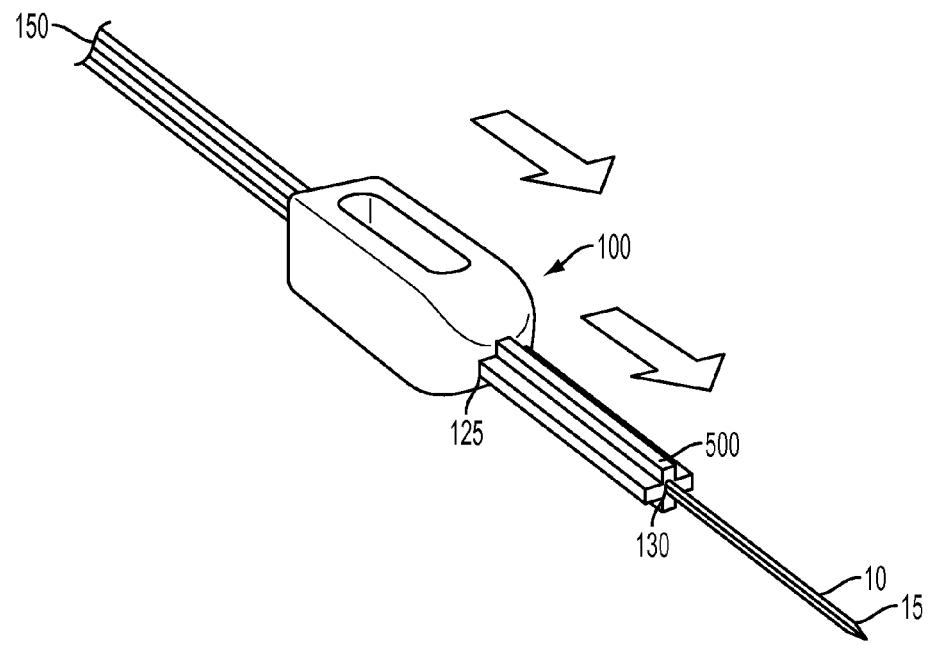
FIG. 4 is a perspective view of an intervertebral cage being delivered over an alternative insertion member, placed over a Kirschner wire, according to various aspects.
Figure 5:
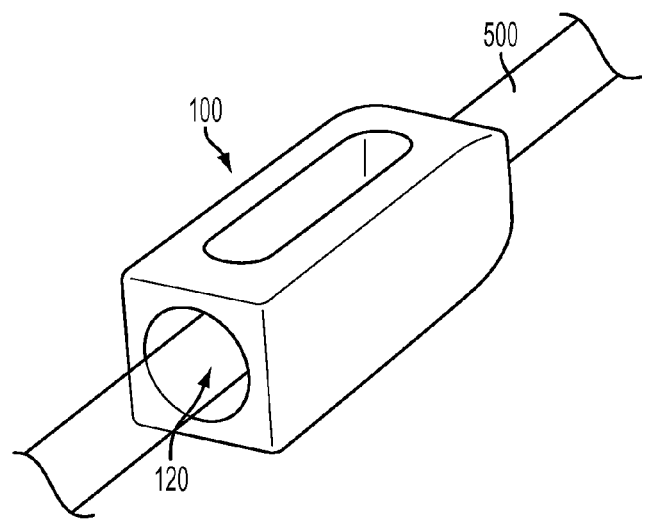
FIG. 5 is a perspective view of a cage assembly being delivered over an alternative insertion member, according to various aspects.

In a further aspect, the insertion member 400, 500, the distal opening and/or the interior channel 120 of the cage body 110 can have a shape configured to prevent or restrict rotation of the cage body relative to the insertion member. A portion of the cage body 110 such as the interior channel, the distal opening and/or the proximal opening, can have a similar shape (thought slightly larger in size) as the cross-sectional shape of the insertion member so that rotation of the cage body relative to the insertion member is restricted. In one aspect, the interior longitudinal channel 120 can be configured for a mating keyed relationship with the elongate insertion member. In another aspect, the cross-sectional shape of the insertion member can be substantially non-circular. For example, the insertion member can be a substantially diamond or rail-shaped insertion member 400 as shown in FIG. 2. In another example, the insertion member 500 can be cross-shaped when viewed in cross-section, as shown in FIG. 4. Other non-circular insertion member cross-sectional shapes are contemplated to work in a similar manner to: 1) restrict rotation between the cage body 100 and the insertion member 400, 500; 2) provide a blunt tip to prevent inadvertent passage out of the disc space; and 3) provide guidance of the cage body 110 into the disc space in the desired location and orientation.

In one aspect, the insertion member 400, 500 can be substantially rigid and formed from metallic materials, such as stainless steel, titanium and the like, polymeric materials such as polyether ether ketone and the like, carbon fiber and/or ceramic materials.

In one aspect, a bore 128 can be defined in a portion of the insertion member 400, 500. In another aspect, the bore can be a longitudinal bore extending from a distal end 144 to a proximal end 146 of the insertion member 400, 500. In still another aspect, the cross-sectional profile of the bore 128 can be similar to the cross-sectional profile of the guide wire 10. In another aspect, the cross-sectional profile of the bore 128 can be slightly larger than the cross-sectional profile of the guide wire 10 so that at least a portion of the guide wire can slide through the bore 128.

In use, in one aspect, a distal end 12 of the guide wire 10 can be positioned as desired in the disc space. The bore 128 of the insertion member 400, 500 can be positioned around the opposed end of the guide wire and at least a portion of the insertion member can be threaded onto the guide wire. The insertion member 400, 500 can then be urged along the guide wire 10 until the distal end 144 of the insertion member is in the desired position in the disc space. That is, the insertion member 400, 500 can be slidably attachable and/or slidably coupled to the guide wire 10. The insertion member 400,500 can then be urged along the guide wire 10 until the insertion member 400, 500 is in the desired position in the disc space.

In another aspect, the insertion member 400, 500 can be rotated relative to the guide wire 10 until the insertion member is at the desired orientation relative to the disc space. Optionally, after the insertion member 400, 500 is in the desired position and orientation, the guide wire 10 may be removed—thereby reducing the risk of the guide wire pushing through the disc annulus, potentially causing injury to organs or vascular structure.

Figure 3:
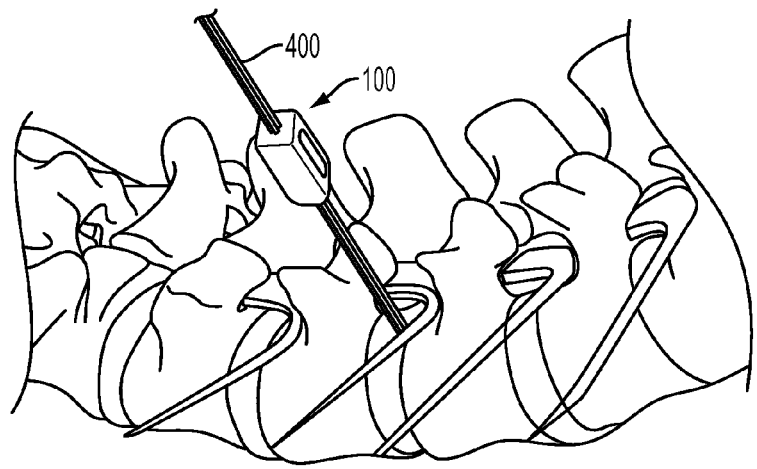
FIG. 3 is a perspective view of an intervertebral cage being delivered over an insertion member toward an intervertebral space, according to various aspects.

The distal opening of the intervertebral cage 100 can be positioned around the proximal end 146 of the insertion member 400, 500 and the intervertebral cage can be threaded onto the insertion member. That is, the intervertebral cage 100 can be slidably attachable and/or slidably coupled to the insertion member. The intervertebral cage 100 can then be urged along the insertion member 400, 500 until the intervertebral cage is in the desired position in the disc space. The profiles of the insertion member, the distal opening and/or the interior channel 120 of the intervertebral cage 100, can prevent rotation of the cage body relative to the insertion member, so that as long as the insertion member 400, 500 is at the desired orientation relative to the disc space, then the intervertebral cage 100 must be at the desired orientation relative to the disc space. Oblique delivery of the intervertebral cage 100 is illustrated in FIGS. 3 and 4.

In another aspect, the insertion member 400, 500 can be used without the guide wire to position the intervertebral cage 100 into the disc space. In this aspect, the distal end 144 of the substantially rigid insertion member 400, 500 can be positioned as desired in the disc space. The distal opening of the intervertebral cage 100 can be positioned around the proximal end 146 of the insertion member 400, 500 and the intervertebral cage can be threaded onto the insertion member. That is, the intervertebral cage 100 can be slidably attachable and/or slidably coupled to the insertion member. The intervertebral cage 100 can then be urged along the insertion member 400, 500 until the intervertebral cage is in the desired position in the disc space.

Thus, the guide wire 10 and the insertion member 400, 500 can be independent, or can be unitized to act together during and after insertion. Optionally, the guide wire 10 and or the insertion member can pass through at least one side channel or a central channel of the cage body.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. An intervertebral space insertion system comprising:
   a body defining an interior longitudinal channel extending from a proximal opening to a distal opening;
   a guide wire having a distal end, a longitudinal length and a cross-sectional profile; and
   an elongate insertion member having a proximal end and a distal end and defining a longitudinal bore configured for receipt of the guide wire, wherein the cross-sectional profile of the bore is similar to the cross-sectional profile of the guide wire, wherein the insertion member has a non-circular cross-sectional shape substantially similar to and matingly engagable with a portion of the interior longitudinal channel of the body,
   wherein the guide wire is insertable through the longitudinal bore and disposed along an axis that is substantially coaxial with the interior longitudinal channel of the body such that the insertion member is slidably attachable to the guide wire, wherein the insertion member is insertable through the interior longitudinal channel of the body such that the body is slidably attachable to the insertion member, wherein when slidably attached, the distal opening of the body surrounds the cross-sectional shape of the insertion member, wherein the distal end of the guide wire is positionable in a desired location in the intervertebral space for guiding the insertion member to the desired location, and wherein the distal end of the insertion member is positionable in the desired location in the intervertebral space for guiding the body to the desired location.

2. The insertion system of claim 1, wherein the cross-sectional shape of the insertion member is substantially diamond-shaped.

3. The insertion system of claim 1, wherein the cross-sectional shape of the insertion member is substantially cross-shaped.

4. The insertion system of claim 1, wherein the cross-sectional shape of the insertion member is substantially similar to and configured to mate with at least one of a cross-sectional shape of the interior longitudinal channel and the shape of the distal opening of the body.

5. The insertion system of claim 4, wherein the longitudinal channel of the body has a cross-sectional shape that is substantially different than the shape of the distal opening of the body.

6. The insertion system of claim 1, wherein the insertion member is substantially rigid.

7. The insertion system of claim 1, wherein the insertion member is slidably, rotatably attachable to the guide wire such that the insertion member is rotatable to a desired orientation relative to the desired location in the intervertebral space.

8. The insertion system of claim 1, wherein the distal end of the insertion member comprises a blunt tip configured to prevent inadvertent passage of the distal end of the insertion member out of the intervertebral space.

9. The insertion system of claim 1, wherein the elongate insertion member is linear and wherein the elongate insertion member is substantially rigid.

10. An intervertebral space insertion system comprising:
    a guide wire having a distal end, a longitudinal length and a cross-sectional profile;
    an elongate insertion member having a proximal end and a distal end and defining a longitudinal bore configured for receipt of the guide wire, the elongate insertion member comprising a non-circular cross-sectional shape; and
    an intervertebral cage defining an interior longitudinal channel configured for a mating keyed relationship with a portion of the elongate insertion member, wherein the guidewire is disposed along an axis that is substantially coaxial with the interior longitudinal channel, wherein the cage is slidably attachable to the insertion member, and wherein when slidably attached, the interior longitudinal channel of the cage surrounds the cross-sectional shape of the insertion member.

11. The insertion system of claim 10, wherein the cross-sectional shape of the insertion member is substantially diamond-shaped.

12. The insertion system of claim 10, wherein the cross-sectional shape of the insertion member is substantially cross-shaped.

13. A method of inserting an intervertebral cage into an intervertebral space, the method comprising:
providing an intervertebral cage having a cage body defining an interior longitudinal channel and a distal opening in the cage body, wherein the distal opening has an opening shape, and wherein the longitudinal channel has a cross-sectional shape;
providing a guide wire having a proximal end, a distal end, a longitudinal length and a cross-sectional profile;
providing an elongate insertion member having a proximal end and a distal end and defining a longitudinal bore configured for receipt of the guide wire, wherein the cross-sectional profile of the longitudinal bore is similar to the cross-sectional profile of the guide wire, wherein the insertion member has a non-circular cross-sectional shape similar to at least one of the opening shape of the distal opening and the cross-sectional shape of the longitudinal channel, wherein the insertion member is configured to be at least partially inserted through the longitudinal channel;
positioning the distal end of the guide wire in a desired location in the intervertebral space;
inserting the proximal end of the guide wire through the longitudinal bore of the insertion member, and urging the distal end of the insertion member to the desired location;
inserting the insertion member through the longitudinal channel of the cage body such that the distal opening of the cage body surrounds the cross-sectional shape of the insertion member and such that the guidewire is disposed along an axis that is substantially coaxial with the longitudinal channel; and
urging the cage body to the desired location.

14. The method of claim 13, wherein the cross-sectional shape of the insertion member is substantially diamond-shaped.

15. The insertion system of claim 13, wherein the cross-sectional shape of the insertion member is substantially cross-shaped.

16. The method of claim 13, wherein the opening shape of the cage body is different than the cross-sectional shape of the longitudinal channel.

17. The method of claim 13, further comprising removing the guide wire after the distal end of the insertion member is in the desired location and before the step of urging the cage body to the desired location.

18. The method of claim 13, wherein the distal end of the insertion member comprises a blunt tip configured to prevent inadvertent passage of the distal end of the insertion member out of the intervertebral space.

* * * * *